US006350588B1

(12) United States Patent
Roth et al.

(10) Patent No.: US 6,350,588 B1
(45) Date of Patent: Feb. 26, 2002

(54) TEST MEDIA AND QUANTITATIVE OR QUALITATIVE METHOD FOR IDENTIFICATION AND DIFFERENTIATION OF BIOLOGICAL MATERIALS IN A TEST SAMPLE

(75) Inventors: Geoffrey N. Roth; Jonathan N. Roth, both of Goshen, IN (US)

(73) Assignee: Micrology Laboratories, LLC, Goshen, IN (US)

(*) Notice: Subject to any disclaimer, the term of this patent is extended or adjusted under 35 U.S.C. 154(b) by 0 days.

(21) Appl. No.: 09/357,606

(22) Filed: Jul. 20, 1999

(51) Int. Cl.[7] ............................. C12Q 1/04; C12Q 1/10; G01N 33/569; G01N 1/54

(52) U.S. Cl. .......................... 435/34; 435/38; 435/7.32; 435/14

(58) Field of Search ........................... 435/34, 7.32, 38, 435/7.35, 7.37, 252.4, 252.8, 14

(56) References Cited

U.S. PATENT DOCUMENTS

| | | | | |
|---|---|---|---|---|
| 4,308,348 A | * | 12/1981 | Monget | 435/38 |
| 5,093,239 A | * | 3/1992 | Belly et al. | 435/34 |
| 5,210,022 A | | 5/1993 | Roth et al. | 435/34 |
| 5,358,854 A | | 10/1994 | Ferguson | 435/14 |
| 5,364,767 A | | 11/1994 | Flowers et al. | 435/39 |
| 5,393,662 A | | 2/1995 | Roth et al. | 435/38 |
| 5,443,963 A | | 8/1995 | Lund | 435/34 |
| 5,541,082 A | | 7/1996 | Botchner | 435/34 |
| 5,643,743 A | * | 7/1997 | Chang et al. | 435/34 |
| 5,726,031 A | | 3/1998 | Roth et al. | 435/34 |
| 5,786,167 A | * | 7/1998 | Tuompo et al. | 435/34 |
| 5,837,482 A | * | 11/1998 | Mach et al. | 435/34 |
| 5,888,760 A | * | 3/1999 | Godsey et al. | 435/34 |
| 5,962,251 A | | 10/1999 | Rambach | 435/34 |
| 5,989,892 A | * | 11/1999 | Nishimaki et al. | 435/252.1 |
| 6,008,008 A | * | 12/1999 | James et al. | 435/34 |

FOREIGN PATENT DOCUMENTS

| | | | |
|---|---|---|---|
| EP | 0122028 A1 | 10/1984 | C12Q/1/00 |
| WO | WO 95/04157 | 2/1995 | C12Q/1/104 |
| WO | WO 96/40980 | 12/1996 | C12Q/1/04 |
| WO | WO 98/55644 | 12/1998 | C12Q/1/10 |

OTHER PUBLICATIONS

Sartory et al. A simple membrane enumeration medium for coliforms and *E. coli* utilizing a chromogenic glucuronide substrate. Proc.–Water Qual. technol. Conf. (1993), volume date 1992, (Pt. 2), pp. 1661–1673, Abstract only.*
McDaniels et al. Confirmational identification of *Eschericia coli*, a comparison of genotypic and phenotypic assays for glutamate decarboxylase and beta–D–glucuronidase. (Sep. 1996) Appl. Environ. Microbiol. 62 (9), pp. 3350–3354.*

"Detection of Specific Bacterial Enzymes by High Contrast Metal Chelate Formation Part II. Specific Detection of Escherichia–Coli on Multipoint–Inoculated Plates Using 8 Hydroxyquinoline–Beta–D–Glucuronide" James, A L et al., Zentralblatt Fuer Bakteriologie Mikrobiologie und Hygiene Series A, vol. 267, No. 3, 1988, pp. 316–321—whole document.
Copy of International Search Report as Issued on Dec. 19, 2000 for Corresponding PCT Application No. PCT/US00/19737.
A New Plate Medium for Rapid Presumptive Identification and Differentiation of Enterobacteriaceae, M.Manafi and M.L. Rotter, International Journal of Food Microbioloty, 14 (1991) 127–134 1991.
Microbiological Quality of Natural Waters, Juan J. Borrego, M. Jose Figueras, Microbiologia Sem 13 (1997), 413–426.
Fluorogenic and Chromogenic Enzyme Substrates in Culter Media and Identification Tests, M. Manafi, International Journal of Food Microbiology 31 (1996) 45–48.
A New Membrane Filtration Medium for Simultaneous Detection and Enumeration of *Escherichia coli* and Total Coliforms, M.A. Grant, Applied and Environmental Microbiology, Sep. 1997, p. 3526–3530.
Fluorogenic and Chromogenic Substrates Used in Bacterial Diagnostics, Mohammed Manafi, Wolfgang Kneifel and Shoshana Bascomb, Microbiological Reviews, Sep. 1991, p. 335–348.
E*Colite—Single Step Presence Absence of Coliforms and/or *E. coli*; ColiGel—Single Step Enumeration of Coliforms, and/or *E. coli*, 1996 Charm Sciences, Inc.
Accentuate the Positive, Dr. Laawrence Restaino, Food Quality, Nov./Dec. 1996.

(List continued on next page.)

*Primary Examiner*—Michael P. Woodward
(74) *Attorney, Agent, or Firm*—Baker & Daniels

(57) ABSTRACT

A test medium and method for detecting, quantifying, identifying and differentiating up to four (4) separate biological materials in a test sample. A test medium is disclosed which allows quantifying and differentiating under ambient light aggregates of biological entities producing specific enzymes, which might include general coliforms, *E. coli*, Aeromonas, and Salmonella or Shigella in a single test medium. A new class of nonchromogenic substrate is disclosed which produce a substantially black, non-diffusible precipitate. This precipitate is not subject to interference from other chromogenic substrates present in the test medium. In a preferred form, the substrates are selected such that *E. coli* colonies present in the test medium show as substantially black, general coliforms colonies show in the test medium as a blue-violet color, Aeromonas colonies present in the test medium show as a generally red-pink color, and Salmonella or Shigella colonies show as a generally teal-green color. Other microorganisms and color possibilities for detection and quantification thereof are also disclosed. An inhibitor and method for making a test medium incorporating the inhibitor are disclosed.

3 Claims, No Drawings

OTHER PUBLICATIONS

Evaluation of Cyclohexenoesculetin–B–D Galactoside and 8–Hydroxyquinolin–B–D–Galactoside as Substrates for the Dection of B–Galactosidase, A.L. James, J.D. Perry, M. Ford, L. Armstrong and F.K. Gould, Applied and Environmental Microbiology, Oct. 1996, p. 3868–3870.

New Medium for Simultaneous Detection of Total Coliforms and *Escherichia coli* in Water, K.P. Brenner, C. C. Rankin, Y. R. Roybal, G.N. Stelma, Jr. P.V. Scarpino and A.P. Dufour, Applied and Evniromental Microbiology, Nov. 1993, p. 3534,3544.

Comparison of Several New Chromogenic Galactosides as substrates for various B–D–galacttosidases, I. Pocsi, S.A. Taylor, A.C. Richardson, B.V. Smith and R.G. Price, Biochimica et Biophysica Acta, 1163 (1993) 54.

Rapid Diagnosis of Enterobacteriaceae, M. Kilian and P. Bulow, Acta Path. microbiol. scand. Sect. B, 84: 245–251, 1976.

Fluorogenic Substrates for Differentiation of Gram–Negative Nonfermentative and Oxidase–Positive Fermentative Bacteria, peter Kampfer, Isolde Kulies and Wolfgang Dott, Journal of Clinical Microbiology, Jun. 1992, p. 1402–1406.

Glycosidase Profiles of Members of the Family Enterobacteriaaceae, P. Kampfer, O. Rauhoff and W. Dott, Journal of Clinical Mocrobiology, Dec. 1991, p. 2877–1879.

The Occurrence of Aeromonas species in Drinking Water Supplies of an Area of the Dolomite Mountains, Italy, P. Legnani, E. Leoni, F. Soppeisa and R. Burigo, Journal of Applied Microbiology 1998, 85, 271–276.

Failure of the Most–Porbable–Number Technique to Detect Coliforms in Drinking Water and Raw Water Supplies, T.M. Evans, C.E. Waarvick, R.J. Siedler and M.W. LeChevallier, Applied and Evnironmental Microbiology, Jan. 1981, P. 130–138.

False–Positive Coliform Reaction Mediated by Aeromonas in the Colilert Defined Substrate Technology System, J.P.B. Landre, A.A. Gavriel and A.J. Lamb, Letters in Applied Microbioloty 1998 26, 352–354.

Population Dynamics of Aeromonas spp. in an Urban River, G.W. Pettibone, Applied Microbiology 1998,85, 723–730.

The Effect of Oxidase Positive Bacteria on Total Coliform Density Estimates, L. Lupo, E. Strickland, A. Dufour, V. Cabelli, Health Lab Sci Apr. 1977; 14(2): 117–21 (Abstract only).

Membrane Filtration Differenttiation of *E.. coli* from Coliforms in the Examination of Water, A. Mates, M. Shaffer, Journal of Applied Bacteriology 1989, 67, 343–346.

Comparison of Selective Agars for the Isolation and Identification of Klebesiella Oxytoca and *Escherichia Coli* from Environmental Drinking Water Samples, P.J. Packer, C.W. Mackerness, M. Riches and C.W. Keevil, Letters in Applied Microbiology 1995, 20, 303–307.

Potential Pathogens in the Environment: Cultural Reactions and Nucleic Acid Studies on Klebsiella Pneumoniae from Clinical and Environmental Sources, R.J. Seidler, M.D. Knittel and C. Brown, Applied Microbiology, Jun. 1975, p. 819–825.

Detection of Specific Bactgerial Enzymes by High Contrast Metal Chelate Formation, Part I. 8–Hydroxquinoline–beta–D–glucoside, an Alternative to Aesculin in the Differentiattion of Members of the Family Enterobacteriaceae, James AL, Yeoman P, Zentralbl Bakeriol Mikrobiol Hyg [A] Dec. 1987: 267(2:188–193 (Abstract only).

Microbiological Quality of Natural Waters, J.J. Borrego, M.J. Figueras, Microbiologia Sem 13 (1997), 413–426.

Evaluation of a New Dipslide with Selective Medium for the Rapid Detection of Beta–Glucuronidase–Positive *Escherichia coli*, Larinkari U. Rautio M., Eur J. Clin Microbiol Infect Dis. Jul. 1995: 14(7): 606–9 (Abstract only).

Evaluation of a New Agar in Uricult–Trio for Rapid Detection of *Escherichia Coli* in Urine, Dalet F. Segovia T, J. Clin. Microbiol May 1995; 33(5): 1395–8 (Abstract only).

Detection of Specific Baceterial Enzymes by High Contrast Metal Chelate Formation, Part II. Specific Detection of *Escherichia Coli* on Multipoint–Inoculated Plates Using 8–Hydroxyquinoline–beta–D–Glucuronide, James AL, Yeoman P, Zentralbl Bakteriol Mikrobiol Hyg [A] Jan. 1998: 267(3):316–21 (Abstract only).

Cyclohexenoesculetin–beta–D–Glucoside: A New Substrate fort the Detection of Bacterial beta–D–Glucosidase, James AL, Perry JD, Ford M., Armstrong L., Gould FK, J. Appl. Microbiol Apr. 1997; 82(4):532–6 (Abstract only).

ABC Medium, a New Chromogenic Agar for Selective Isolation of Salmonella spp., J.D. Perry, M. Ford, J.Taylor, A.L.Jones, R. Freeman, F.K.Gould, Journal of Clinical Microbiology, Mar. 1999, p. 766–768.

\* cited by examiner

TEST MEDIA AND QUANTITATIVE OR QUALITATIVE METHOD FOR IDENTIFICATION AND DIFFERENTIATION OF BIOLOGICAL MATERIALS IN A TEST SAMPLE

BACKGROUND OF THE INVENTION

The present invention relates to a test medium and method for the detection, quantification, identification and/or differentiation of biological materials in a sample which may contain a plurality of different biological materials.

Bacteria are the causative factor in many diseases of humans, higher animals and plants, and are commonly transmitted by carriers such as water, beverages, food and other organisms. The testing of these potential carriers of bacteria is of critical importance and generally relies on "indicator organisms." Borrego et al., Microbiol. Sem. 13:413–426, (1998). For example, *Escherichia coli* (*E. coli*) is a gram negative member of the family Enterobacteriaceae which is part of the normal intestinal flora of warm blooded animals, and its presence indicates fecal contamination (e.g., raw sewage). Even though most strains of *E. coli* are not the actual cause of disease, their presence is a strong indication of the possible presence of pathogens associated with intestinal disease, such as cholera, dysentery, and hepatitis, among others. Consequently, *E. coli* has become a prime indicator organism for fecal contamination, and as a result, any method which differentiates and identifies *E. coli* from other bacteria is very useful.

Others members of the family Enterobacteriaceae, commonly referred to as "general coliforms," especially the genera Citrobacter, Enterobacter and Klebsiella, are also considered to be significant indicator organisms for the quality of water, beverages and foods. Therefore, tests to identify and differentiate general coliforms from *E. coli* are also very useful. Also, various species of the genus Aeromonas have been shown to not only be potential pathogens, but to have a correlation to other indicator organisms (Pettibone et al., *J. App. Microbiol.* 85:723–730 (1998)). Current test methods to identify, separate and enumerate Aeromonas spp. from the very similar Enterobacteriaceae have been lacking and most of the current methods utilizing enzyme substrates do not separate Aeromonas spp. from Enterobacteriaceae due to their almost identical biochemical profiles. Any method that depends upon the identification of general coliforms by means of a β-galactosidase substrate either does not differentiate Aeromonas spp. from general coliforms or eliminates Aeromonas from the sample by the use of specific inhibitors (antibiotic such as cefsulodin). Brenner et al., *Appl. Envir. Microbio.* 59:3534–44 (1993). They do not differentiate, identify and enumerate Aeromonas along with *E. coli* and general coliforms. Landre et al., *Letters Appl. Microbiol.* 26:352–354(1998). Improved test methods to effectively identify, separate and enumerate such bacterial types are needed, and there is a continuing search for faster, more accurate, easier to use and more versatile test methods and apparatus in this area.

Numerous test methods have been utilized to determine, identify and enumerate one or more indicator organisms. Some of these test methods only indicate the presence or absence of the microorganism, while others also attempt to quantify one or more of the particular organisms in the test sample. For example, a qualitative test referred to as the Presence/Absence (or P/A) test, may be utilized to determine the presence or absence of coliforms and *E. coli* in a test sample. A test medium including the β-galactosidase substrate O-nitrophenyl-β-D-galactopyranoside (ONPG), and the β-glucuronidase substrate 4-methyl-umbrelliferyl-β-D-glucuronide (MUG), is inoculated with the test sample. To differentiate the general coliforms from *E. coli,* this test relies on the fact that generally all coliforms produce β-galactosidase, whereas only *E. coli* also produces β-glucuronidase in addition to β-galactosidase. If any coliforms are present (including *E. coli*), the broth medium turns a yellow color due to the activity of the galactosidase enzyme on the ONPG material, causing the release of a diffusible yellow pigment. If *E. coli* is present, the broth medium will demonstrate a blue fluorescence when irradiated with ultraviolet rays, due to the breakdown of the MUG reagent with the release of the fluorogenic dye caused by the production of the glucuronidase enzyme. These reactions are very specific, and allow the presence of both coliforms in general, as well as *E. coli* to be identified in a single sample. A disadvantage of this test is that it is not directly quantitative for either bacterial type, since both reagents produce diffusible pigments. A second disadvantage is that there may a false positive coliform reaction if Aeromonas spp. are present in the test sample. This has been shown to be possible even when there are inhibitors present to supposedly prevent this from occurring (Landre et al., *Letters Appl. Microbiol.* 26:352–354 (1998)). The test also requires specific equipment for producing the ultraviolet rays. Further, this test may only be used to detect coliforms and *E. coli.* Other important microorganisms, such as the strain *E. coli* 0157 which is glucuronidase negative, are not detected, nor are other non-galactosidase-glucuronidase producing microorganisms.

The Violet Red Bile Agar (VRBA) method has been used to determine the quantity of both coliform and *E. coli* in a test sample. The test medium used in this method includes bile salts (to inhibit non-coliforms), lactose and the pH indicator neutral red. As coliforms (including *E. coli*) grow in the medium, the lactose is fermented with acid production, and the neutral red in the area of the bacterial colony becomes a brick red color. The results of this test are not always easy to interpret, and in order to determine the presence of *E coli,* confirming follow-up tests, such as brilliant green lactose broth fermentation, growth in EC broth at 44.5° C. and streaking on Eosin Methylene Blue Agar (EMBA), must be performed.

The Membrane Filter (MF) method utilizes micropore filters through which samples are passed so that the bacteria are retained on the surface of the filter. This method is used most often when bacterial populations are very small, and a large sample is needed to get adequate numbers. The filter is then placed on the surface of a chosen medium, incubated, and the bacterial colonies growing on the membrane filter surface are counted and evaluated. This method is widely used and provides good results when combined with proper reagents and media A disadvantage of this method is that it is expensive and time-consuming. It also does not work well with solid samples, or samples with high particulate counts. The MF method can be used in conjunction with the inventive method described in this application.

The m-Endo method is also used to determine the quantity of *E. coli* and general coliforms and is an official USEPA approved method for testing water quality. The medium is commonly used with a membrane filter and *E. coli* and general coliform colony forming units (CFU) grow as dark colonies with a golden green metallic sheen. Due to a proven high rate of false positive error, typical colonies must be confirmed by additional testing. *Standard Methods for the Examination of water and Wastewater,* 20$^{th}$ Edition, 9–10 &9–60 (1998).

Other tests, such as the Most Probable Number (MPN), utilize lactose containing broths (LST, BGLB, EC) to estimate numbers of general coliforms and *E. coli*, but have also been shown to have high rates or error as well as being cumbersome and slow to produce results. Evans et al., *Appl. Envir. Microbiol* 41:130–138 (1981).

The reagent 5-bromo-4-chloro-3-indolyl-β-D-galactopyranoside (X-gal) is a known test compound for identifying coliforms. When acted on by the β-galactosidase enzyme produced by coliforms, X-gal forms an insoluble indigo blue precipitate. X-gal can be incorporated into a nutrient medium such as an agar plate, and if a sample containing coliforms is present, the coliforms will grow as indigo blue colonies. X-gal has the advantage over the compound ONPG, described above, in that it forms a water insoluble precipitate rather than a diffusible compound, thereby enabling a quantitative determination of coliforms to be made when the test sample is incorporated into or onto a solidified medium, or when coliform colonies grow on the surface of a membrane filter resting on a pad saturated with a liquid medium or on a membrane filter resting on a solid medium. Further, it does not require the use of ultraviolet light.

A similar compound, 5-bromo-4-chloro-3-indolyl-β-D-glucuronide (X-gluc) is a known test compound for identifying *E. coli*. When acted on by the β-glucuronidase enzyme produced by most *E. coli*, X-gluc forms an insoluble indigo blue precipitate. X-gluc has the advantage over the compound MUG, described above, in that it forms a water insoluble precipitate, rather than a diffusible compound, thereby enabling a quantitative determination of *E. coli* to be made when the test sample is incorporated into or onto a solidified medium. X-gluc and its ability to identify *E. coli* are described in Watkins, et al., *Appl. Envir. Microbiol.* 54:1874–1875 (1988). A similar compound, indoxyl-β-D-glucuronide, which also produces sharp blue colonies of *E. coli*, was described in Ley, et al., *Can. J. Microbiol.* 34:690–693 (1987).

Although X-gal and X-gluc are each separately useful in the quantitative determination of either coliforms (X-gal) or *E. coli* (X-gluc), these indicator compounds have the disadvantage that they each contain the same chromogenic component. Therefore, they cannot be used together to identify and distinguish both *E. coli* and general coliforms in a single test with a single sample, since they both generate identically hued indigo blue colonies. A person using both reagents together would be able to quantitatively identify the total number of coliforms, the same as if X-gal were used alone, but would not be able to indicate which of the colonies were *E. coli* and which were other coliforms besides *E. coli*.

A recently developed and highly commercially successful test method and test medium for quantitatively identifying and differentiating general coliforms and *E. coli* in a test sample is described in U.S. Pat. Nos. 5,210,022, and 5,393,662, both of which share common inventorship with the present application and which are hereby incorporated by reference. This method and test medium improves upon prior art methods by allowing the quantitative identification of general coliforms and *E. coli* in a single sample. Additional confirmatory tests are not necessary. The test sample is added to a medium containing a galactosidase substrate, such as 6-chloroindolyl-β-D-galactoside, and a β-glucuronidase substrate, such as 5-bromo-4-chloro-3-indolyl-β-D-glucuronide (X-gluc). The β-galactosidase substrate is capable of forming a water insoluble precipitate of a first color upon reacting with β-galactosidase, and the β-glucuronidase substrate is capable of forming a water insoluble precipitate of a second color, contrasting with the first color, upon reacting with β-glucuronidase. As a result, general coliforms may be quantified by enumerating the colonies of the first color (having β-galactosidase activity), and *E. coli* may be quantified by enumerating the colonies of the second color (having both β-galactosidase and β-glucuronidase activity). This technology has been widely copied.

Another recently developed test method and apparatus provides excellent results for the differentiation and identification of general coliforms, *E. coli* and *E. coli* 0157 strains and non-coliform Enterobacteriaceae. The method and test medium are described in U.S. Pat. No. 5,726,031, which shares common inventorship with the present application, and which is hereby incorporated by reference.

A certain class of substrates, referred to herein as "nonchromogenic," have been used to detect various microorganisms. A dipslide for detecting *E. coli* using hydroxyquinoline-β-D-glucuronide is disclosed by Dalet et al., *J. Clin. Microbiol,* 33(5):1395–8 (1995). Similarly, a technique for detection of *E. coli* in an agar-based medium using 8-hydroxyquinoline-β-D-glucuronide is disclosed by James et al., *Zentralbl Bakteriol Mikrobiol Hyg [A],* 267(3):316–21 (1988).

It is desirable to further improve the distinguishing colors generated in the test media. That is to say, in prior art test media which detect and distinguishing two biological entities, confusion may arise between the two colors which show in the media.

Further, it is desirable to be able to identify and differentiate other closely related organisms, such as members of the families Aeromonaceae, Vibrionaceae, and Salmonella and Shigella spp. For example, the genus Aeromonas is closely related to coliforms and gives an almost identical biochemical test pattern. Further, the genus Vibrio is also an important type of bacteria that grows under the same general conditions as coliforms. It is known to distinguish Aeromonas colonies from general coliforms by testing all colonies in a given sample for the presence of cytochrome oxidase. Undesirably, however, this requires another set of tests. Further, Aeromonas is common in water and food, and it is commonly indicated in test samples as general coliforms, which results in high a false positive error for general coliforms by most current test methods. The Aeromonas can be prevented from interfering with the coliform results by adding certain antibiotics to the medium. However, the antibiotic amounts added must be carefully controlled. Further, the antibiotics which have been conventionally used have short life spans in the media so that they lose their potency quickly in other than a frozen condition. It may often be desirable to be able to culture, identify and enumerate Aeromonas spp. which cannot be done if they are inhibited.

Further, in those cases where it is desirable to inhibit Aeromonas, it is desirable for a better method of so doing, one in which the shelf life of the medium is not appreciably reduced by the inclusion of an inhibitor.

Additionally, it is also desirable to distinguish strains of Salmonella and Shigella from *E. coli,* general coliforms and Aeromonas.

SUMMARY OF THE INVENTION

The present invention overcomes the disadvantages of prior art methods by providing a test method and medium for quantitatively or qualitatively identifying and differentiating biological entities in a test sample that may include a plurality of different biological entities.

The present invention introduces the use of "nonchromogenic" substrates to enhance the distinction among multiple colors produced by distinct biological entities present in the inventive test medium. Unexpectedly, it has been discovered that other "chromogenic" substrates present in the inventive test medium do not interfere with the substantially black color achieved with the nonchromogenic substrate. That is to say, so long as a given biological entity is responsive to the nonchromogenic substrate, aggregations thereof present in the test medium will show as a substantially black color-independent of whether such biological entity is responsive to one, two or more chromogenic substrates which are also present in the medium. The present invention exploits this hitherto unexplored property of nonchromogenic substrates.

In one form thereof, the present invention provides a test medium for detecting, identifying and qualifying or quantifying first and second biological entities. The test medium includes a nutrient base medium including ions of a salt, a chromogenic substrate and a nonchromogenic substrate. The first biological entity is responsive to the nonchromogenic substrate whereas the second biological entity is responsive to the chromogenic substrate. In this test medium, aggregations of the first biological entity present in the test medium are substantially black and aggregations of the second biological entity present in the test medium are a second color, the second color being distinguishable from the substantially black.

In a preferred form, the inventive test medium accounts for the first biological entity being responsive to the chromogenic substrate in addition to the nonchromogenic substrate. In such event, aggregations of the first biological entity present in the test medium will nonetheless show as substantially black.

Significantly, even though the aggregations of the first biological entity are responsive to both the first and second substrates in the preferred form, these aggregations still show as substantially black in the test medium. That is, the chromogenic substrate does not interfere with the substantially black color. Advantageously, this property of nonchromogenic substrates allows several different biological entities to be identified and differentiated in a single medium, aggregations of each biological entity having a visually distinguishable color.

In another preferred form of the above-described inventive medium, the medium further includes the antibiotic nalidixic acid to inhibit the growth of Aeromonas, spp. Advantageously, it has been found that nalidixic acid, as compared with cefsulodin, does not significantly reduce the shelf life of the test medium incorporating it.

In this connection, another form of the present invention provides a method of making a test medium for detecting at least one first type of biological entity and inhibiting a second type of biological entity from growing in the medium. The method includes the steps of combining desired substrates with a nutrient base medium; adding an inhibitor to the medium; and then sterilizing the medium by subjecting the medium to at least 100° C. Because the inhibitor is added as an initial step, subsequent sterile addition of inhibitor is unnecessary.

In another form thereof, the present invention provides a test medium for detecting, identifying and qualifying or quantifying first, second and third biological entities. The test medium includes a nutrient base medium including ions of a salt. First and second chromogenic substrates and a nonchromogenic substrate are provided in the test medium. The first and second biological entities are responsive to the first and the second chromogenic substrates, respectively, and the third biological entity is responsive to the nonchromogenic substrate. Aggregations of the first biological entity present in the test medium are a first color, aggregations of the second biological entity present in the test medium are a second color, and aggregations of the third biological entity present in the test medium are substantially black.

In a preferred form, the inventive test medium accounts for the third biological entity being responsive to the first and/or the second chromogenic substrates in addition to the nonchromogenic substrate. In such event, aggregations of the third biological entity will nonetheless show as substantially black.

It should be appreciated that the use of a nonchromogenic substrate along with one or more chromogenic substrates synergistically increases the number of biological entities that can be detected and distinguished in a single medium and synergistically increases the possible color combinations for a given set of biological entities to be detected. Stated another way, including a nonchromogenic component as one of the substrates synergistically increases the degrees of freedom in selecting other substrates and corresponding colors for a test medium. This is so because an aggregation of the biological entity which is responsive to the nonchromogenic substrate will dependably show as substantially black. No combined color effects need be accounted for with the nonchromogenic substrates. For example, in a test medium including three chromogenic substrates and a nonchromogenic substrate, at least three combined color combination effects are avoided by using the one nonchromogenic component, as compared with using four chromogenic components.

The present invention, in another form thereof, provides a test medium capable of detecting, quantifying, and differentiating general coliforms and/or $E.$ $coli$ spp. under ambient light. The test medium comprises a nutrient based medium including a salt. A first substrate capable of forming a first water insoluble component of a first color in the presence of $E.$ $coli$ and the ions of the salt is provided in the medium. The first color is substantially black. A second substrate capable of forming a second water insoluble component of a second color in the presence of general coliforms is provided. The second color is visually distinguishable from the first color. Thus, colonies of $E.$ $coli$ present in the test medium are indicated by the first substantially black color and colonies of general coliforms are indicated by the second color.

In a preferred form of the above invention, the test medium further includes a third substrate capable of forming a third water insoluble component of a third color in the presence of Salmonella or Shigella spp. The third color is distinguishable from the first and second colors, whereby the test medium is capable of quantifying and/or differentiating $E.$ $coli,$ general coliforms and Salmonella or Shigella spp. Further, the substrates are selected such that general coliforms present in the test medium will also react with the third substrate to form a water insoluble component which includes the third color. Consequently, general coliform colonies are indicated in the test medium as a fourth color, the fourth color being a combination of the second color and the third color. The fourth color is visually distinguishable from the first and third colors. Still further, the substrates can be selected such that Aeromonas spp. form an insoluble component of the second color by reacting with the second substrate, but not the first and third substrates. Thus, in the inventive test medium, E. coli colonies will be generally black, general coliform colonies will be the fourth color, Aeromonas colonies will be the second color and Shigella or Salmonella colonies will be the third color.

In another form thereof, the present invention provides a method for detecting, quantifying and differentiating under ambient light general coliforms, E. coli, and at least one of the genera Aeromonas, Salmonella or Shigella in a test sample. The method comprises the steps of providing a nutrient base medium including first, second and third substrates. Each of the substrates is capable of forming a water insoluble component in the presence of at least one of general coliforms, E. coli Aeromonas, Salmonella or Shigella. The substrates are selected such that colonies of E. coli produced in the test medium are a first color, colonies of general coliforms produced in the test medium are a second color, and colonies of one of Aeromonas and Salmonella or Shigella produced in the test medium are a third color. Each of the colors are visually distinguishable. The test medium is inoculated with the test sample and then incubated. The test medium is then examined for the presence of first colonies having the first color, second colonies having the second color, and third colonies having the third color. The first colonies are E. coli, the second colonies are general coliforms, and the third colonies are one of Aeromonas, Salmonella or Shigella.

In a preferred form thereof, the inventive method further includes adding ions from a salt to the test medium to react with one or more of the substrates. In so doing, a precipitate is produced which shows as a substantially black color in the presence of the specific enzyme for that substrate. A preferred compound for forming the substantially black color in the presence of the ions of the salt consists of a β-D-glucuronide. These compounds release an aglycone when hydrolized which forms a substantially black insoluble complex in the presence of ions.

In another preferred form of the inventive method, the method further comprises examining the test medium for the presence of fourth colonies having a fourth color, wherein the substrates are selected such that colonies of Aeromonas are the third color and colonies of Salmonella or Shigella are the fourth color, the fourth color being visually distinguishable from the first, the second and the third colors. More preferably, the substrates are selected such that the first color is substantially black, the second color is substantially blue-violet, the third color is substantially red-pink and the fourth color is substantially teal-green.

In another preferred form of the inventive method, the substrates are selected such that colonies of Aeromonas as well as colonies of Plesiomonas and Vibrios are indicated as the third color.

One advantage of the present invention is that it uses a nonchromogenic substrate along with one or more chromogenic substrates and thereby synergistically increases the degrees of design freedom in selecting colors for the inventive test medium. This is so because the chromogenic substrates do not interfere with the substantially black precipitate formed by the nonchromogenic substrate.

Another advantage of the present invention is that enables the quantification, identification and differentiation of four (4) different bacterial strains simultaneously in a single test medium using a single test sample, under ambient lighting. Subsequent tests with their concomitant extra time spent and extra costs are avoided. Of course, the inventive test medium of the present invention could also be used purely for qualitative purposes, as a mere presence/absence (P/A) test.

Yet another advantage of the present invention is that the substrates are selected such that the colors are easy to visually distinguish from one another without the need for UV light or other visual aids, other than, perhaps, magnification means. For example, in a preferred embodiment, E. coli colonies are clearly indicated by a precipitate having a substantially black color, general coliform colonies are indicated by a blue-violet color, Aeromonas colonies are indicated by a red-pink color, and Salmonella or Shigella colonies are indicated by a teal-green color. Because these colors are visually so distinct, confusion among the colors is greatly reduced as compared to prior art media.

Another advantage of the test medium of the present invention is its flexibility and ease of use. The incubation temperature is not critical as growth and differentiation of the organisms mentioned may occur within an optimum range. Therefore, resuscitation steps are avoided and inhibition of temperature sensitive strains does not occur. Also, inexpensive equipment may be used.

Yet another advantage of the present invention is that it intensifies the color distinction obtained in a test medium for identifying and differentiating E. coli from general coliforms. In a preferred test medium, E. coli colonies present a substantially black color, whereas general coliforms present a red-pink color, the distinction therebetween being much more apparent than in prior art test media. Confusion between the two colors is therefore greatly reduced.

Still another advantage of the present invention is that it enables the identification and differentiation of Aeromonas spp. from general coliforms. Prior art test media undesirably require using a cefsulodin inhibitor for preventing Aeromonas spp. from growing therein. However, the use of cefsulodin as an inhibitor requires an extra step in the process, viz., sterile addition of filter sterilized antibiotic, and is difficult to control. Further, the presence of cefsulodin significantly reduces the effective shelf life of the medium. Further, the use of an inhibitor, obviously, prevents the detection and quantitification of Aeromonas spp. Advantageously, with the present invention, Aeromonas spp. can be detected, quantified and differentiated from general coliforms in a single medium.

As a related advantage, if it is nonetheless desired to inhibit colonies of Aeromonas spp. from growing in the test medium, the present invention provides a superior means for doing so. Specifically, preferred forms of the present invention employ nalidixic acid as an inhibitor, which has been shown to have a far less deleterious effect to the shelf-life of the medium incorporating it. Further, nalidixic acid can be added as part of the initial medium formulation prior to sterilization, thereby avoiding a costly and difficult process step which is required with cefsulodin. Finally, nalidixic acid is much less expensive than cefsulodin.

Another advantage of the present invention is that it can provide a test medium for qualitative or quantitative testing. That is, the test media in accordance with the present invention can be used as mere presence/absence test devices, or can be used to quantify various biological entities showing as different colored colonies on the inventive test media.

DETAILED DESCRIPTION OF THE INVENTION

The method and medium of the present invention allow the simultaneous detection, quantification, identification and differentiation of a variety of selected biological entities in a sample of mixed populations of biological entities. The inventive method and medium are particularly useful for the detection, quantification, identification and differentiation of E. coli and general coliforms, and further quantitative identification and differentiation of other selected biological entities, including Aeromonas, Salmonella, Shigella, Pseudomonas, and Vibrio bacterial species.

The method and test media incorporating the present invention utilize the fact that the enzymatic activity of biological entities and specifically of bacteria varies with the genus, and/or family of bacteria of interest. The method and test media incorporating the present invention further utilize the fact that various enzyme identifying substrate complexes can be used to identify specific enzymes with the production of distinctive colors. Significantly, the method and test media incorporating the present invention exploit the fact that chromogenic substrates present in a test medium do not interfere with the substantially black color produced by nonchromogenic substrates.

While nonchromogenic substrates are known in the art, per se, their distinct properties vis-á-vis chromogenic substrates have been unrecognized. However, the behavior of a nonchromogenic substrate in a medium including a combination of chromogenic substrates is unique. To illustrate, aggregations of a biological entity which is responsive to two chromogenic substrates will typically show in a test medium as a combination of the the two colors produced upon cleavage of the two respective substrates. If three chromogenic substrates are involved, the combined color effect could be prohibitively difficult to predict and account for. Further, inherent variations in the amount of enzymes produced by particular strains of biological entities can result in different shades or hues of colors upon cleavage of the chromogenic substrates. Consequently, the colors can be difficult to distinguish for the lay person examining the test medium. Chromogenic substrates must therefore be chosen in view of the other chromogenic substrates planned for inclusion in a given test medium.

Such is not the case with the nonchromogenic components. While aggregations of biological entities which are responsive to chromogenic substrates in addition to nonchromogenic substrates may show in the test medium as having a colored or fluoroescent "halo," such aggregations nonetheless appear substantially black and are therefore easy to identify. Unlike chromogenic substrates, multiple "degrees of freedom" are achieved with the nonchromogenic components by not having to take into account combined color effects.

Using a nonchromogenic substrate enables a single test medium to differentiate four (4) different bacterial strains with four (4) visually distinguishable colors. The black color is superior in that it is difficult to mistake. Further, the substantially black pigmentation does not diffuse so that the location of the colonies is precisely known and the colonies can be accurately counted. The nonchromogenic substrates produce an insoluble chelated compound which is different than the dimer which is produced by the chromogenic substrates.

The inventive test medium and method allows not only a detection, quantification or qualitative identification and differentiation of general coliforms and E. coli, but also of Salmonella, Shigella and Aeromonas, as well as Plesiomonas and Vibrio. Plesiomonas and Vibrios species are determined but not differentiated from Aeromonas species as they are very closely related.

Definitions

Biological entities, such as general coliforms, E. coli., etc., are herein referred to as being "responsive" to certain chromogenic and nonchromogenic substrates. More specifically, a biological entity will predictably produce specific enzymes when the entity is present in a test medium such as the one described hereinbelow. These enzymes will selectively cleave chromogenic and nonchromogenic substrates. Upon cleavage, these substrates produce a color in the test medium. The mechanism for producing the color is different for chromogenic and nonchromogenic substrates, as described hereinbelow.

Microorganisms having β-galactosidase activity include those commonly known by the designation "coliform." There are various definitions of "coliform," but the generally accepted ones include bacteria which are members of the Enterobacteriaceae family, and have the ability to ferment the sugar lactose with the evolution of gas and acid. Most coliforms are positive for both α- and β-galactosidase. That is, they produce both α- and β-galactosidases.

Microorganisms having β-glucuronidase activity in addition to galactosidase activity primarily include most strains of Escherichia coli. That is, E. coli is positive for both α- and β-galactosidase as well as β-glucuronidase.

The term "general coliforms" as used in this application refers to coliforms other than the various strains of E. coli. These "general coliforms" are gram-negative, non-spore forming microorganisms generally having α- and β-galactosidase activity (i.e., lactose fermenters), but not having β-glucuronidase activity, and having the ability to ferment the sugar sorbitol.

For purposes of this specification, a "chromogenic substrate" is a substrate which needs no additional chemicals present in the test medium upon hydrolysis for color production. That is, a chromogenic substrate is cleaved by the specific enzyme corresponding to that substrate to form a dimer with the color being concentrated in the area of cleavage of the substrate. Many chromogenic substrates are known in the art. For purposes of this specification "chromogenic" includes fluorogenic substrates. The products of fluorogenic substrates require ultraviolet (UV) light to be detected and are more soluble than preferred chromogenic substrates, so are therefore generally not preferred for use with the test media disclosed hereinbelow.

Certain substrates, referred to herein as "nonchromogenic," produce a dark, substantially black precipitate in the presence of ions of a salt and enzyme activity. For example, 8-hydroxyquinoline-β-D-glucuronide, when included in a medium along with a salt that produces ions, such as ferric ammonium citrate, will produce a substantially black precipitate in the presence of β-glucuronidase produced by E. coli or other biological entities. More specifically, upon cleavage of the nonchromogenic substrate by the particular enzyme, a substantially black water-insoluble complex forms in the medium. The substantially black precipitate consists of the ferric ions and the aglycone released when the substrate is hydrolized by the glucuronidase from E. coli. This precipitate is a chelated compound which does not diffuse. Nor is the substantially black color susceptible to interference from chromogenic compounds present in the test medium.

For purposes of this specification a "nonchromogenic substrate" means that a chemical in addition to those used with chromogenic components must be present in the test medium when the substrate is cleaved by its corresponding enzyme. The substantially black precipitate formed thereby is a combination of the substrate—salt complex and is not a dimer as is formed by the "chromogenic compounds."

For purposes of this specification, the expression "under ambient light" refers to the visible spectrum, i.e., colors which can be seen and distinguished with the naked eye. A colony present in a test medium which requires ultraviolet light to be seen, for example, would not fall under the definition "under ambient light". However, it is to be understood that the term "under ambient light" includes using a magnification device, if necessary. Magnification can be especially helpful when counting numerous colonies. The term "visually distinguishable" refers to two or more colors which can be differentiated under ambient light.

For purposes of this specification, the term "substantially black" includes dark brown to black, and also includes black with various colored halos, such as red-violet, green, fluorescent, etc.

For further purposes of this specification, color names recited herein are given as guidance, but it is to be understood that the color names are to be read broadly. That is, there can be overlap among the recited colors. This is because, as discussed, biological entities produce varying amounts of enzymes, which in turn affects the shade or hue of the resulting color.

The term "β-galactosidase substrate" as used herein refers to a β-galactoside comprising galactose joined by β-linkage to a substituent that forms a water insoluble colored compound when liberated by the action of β-galactosidase on the substrate. Similarly, the term "α-galactosidase substrate" as used herein refers to α-galactoside comprising galactose joined by α-linkage to a substituent that forms a water insoluble colored compound when liberated by the action of α-galactosidase on the substrate. The term "β-glucuronidase substrate" as used herein refers to a β-glucuronide comprising glucuronic acid joined by β-linkage to a substituent that forms a water insoluble colored precipitate when liberated by the action of β-glucuronidase on the substrate.

The α- and β-galactosidase substrates and compounds and any other substrates described herein as well as the β-glucuronidase substrates and compounds and any other substrates described herein may comprise carboxylate salts formed by reacting a suitable base with the appropriate galactoside or glucuronic carboxyl group. Suitable bases include alkali metal or alkaline earth metal hydroxides or carbonates, for example, sodium hydroxide, potassium hydroxide, calcium hydroxide, magnesium hydroxide, and corresponding carbonates; and nitrogen bases such as ammonia, and alkylamines such as trimethylamine, triethylamine and cyclohexylamine.

Designing a Test Medium for Specific Biological Entities

Certain members of the family Enterobacteriaceae can be distinguished by the presence of α-galactosidase activity in the absence of β-galactosidase activity, or vice-versa. For example, most Salmonella and Shigella spp. are positive for α-galactosidase, but negative for β-galactosidase. Similarly, Aeromonas spp. can be distinguished from other members of the family Enterobacteriaceae by the presence of β-galactosidase activity in the absence of α-galactosidase activity. The method and medium incorporating the present invention are designed to take advantage of these distinguishing characteristics. For example, the specificity of enzyme activity for Salmonella and Aeromonas spp., as opposed to general coliforms, can be exploited, as illustrated below.

The method described herein is particularly suitable for the detection, quantification or qualitative identification and differentiation of the different classes of microorganisms described previously, viz., general coliforms, E. coli, Aeromonas and Salmonella and Shigella spp. Although the inventive method is particularly suitable for these particular microorganisms, it is not limited thereto. Instead, the techniques described herein have application to the identification and differentiation of a wide variety of biological entities.

That is, specific biological entities are "responsive" to various substrates. More particularly, these biological entities predictably produce or contain known enzymes. Substrates, either chromogenic or nonchromogenic, can be selected which, in the presence of a particular enzyme(s), will form an insoluble component of a predictable and distinguishable color. Multiple substrates can be selected to simultaneously identify a plurality of distinct biological entities in a single test medium, aggregations of each distinct entity being identifiable by a separate, distinguishable color. Further, while the preferred embodiments disclosed herein distinguish all of the various aggregations present in a test medium under ambient light, as that term is defined herein, such is not necessary. For example, several substrates disclosed herein require the use of ultraviolet light for the aggregations present in the medium to be seen.

Table I lists various enzymes whose presence may be detected using certain of the substrates listed in Table II.

TABLE I

Enzymes and Abbreviations

| | |
|---|---|
| Aara = α-D-arabinopyranosidase | Bglu = β-D-glucopyranosidase |
| Agal = α-D-galactopyranosidase | Bgluc = β-D-glucuronidase |
| Aglu = α-D-glucopyranosidase | Bman = β-D-mannopyranosidase |
| Bcel = β-D-cellopyranosidase | Bxyl = β-D-xylopyranosidase |
| Bfuc = β-D-fucopyranosidase | Nagal = N-acetyl-β-D-galactopyranosidase |
| Bgal = β-D-galactopyranosidase | Naglu = N-acetyl-β-D-glucopyranosidase |
| Afuc = α-D-fucopyranosidase | Bara = β-D-arabinopyranosidase |
| Bxyl = β-D-xylopyranosidase | Acel = α-D-cellopyranosidase |
| Aman = α-D-mannopyranosidase | Agluc = α-D-glucuronidase |
| Axyl = α-D-xylopyranosidase esterase | Nagluc = N-acetyl-β-D-glucuronidase |

TABLE II

Various Substrates and Color Upon Cleavage

| | |
|---|---|
| 6-chloro-3-indolyl substrates | Pink |
| 5-bromo-4-chloro-3-indolyl substrates | Teal |
| 3-indolyl substrates | Teal |
| N-methylindolyl substrates | Green |
| nitrophenyl substrates | Yellow |
| nitroaniline substrates | Yellow |
| 8-hydroxyquinoline substrates (and ion of salt) | Substantially black |
| cyclohexenoesculetin substrates (and ion of salt) | Substantially black |
| esculetin substrates (and ion of salt) | Substantially black |
| quinoline substrates (and ion of salt) | Substantially black |
| 5-Iodo-3-Indolyl substrates | Purple |
| 5-Bromo-6-Chloro-3-Indolyl substrates | Magenta |
| 6-Fluoro-3-Indolyl substrates | Pink |
| coumarin substrates | Fluorescent |
| fluorescein substrates | Fluorescent |
| rhodamine substrates | Fluorescent |
| resorufun substrates | Fluorescent |

Specific substrate compounds applicable for use with the test medium of the present invention are available as follows:

5-bromo-4-chloro-3-indolyl-β-D-galactopyranoside (X-gal) is a commercially available β-galactosidase substrate that produces an insoluble precipitate having an approximately teal color when reacted upon by β-galactosidase and is available from Biosynth International, Naperville, Ill.

6-chloro-3-indolyl-β-D-glucuronide is a compound which produces an insoluble precipitate having a magenta color, the preparation of which is described in the aforementioned incorporated by reference U.S. Pat. No. 5,210,022 and is available from Research Organics, Cleveland, Ohio.

The compound 5-bromo-4-chloro-3-indolyl-β-D-glucuronide (X-gluc) is a commercially available β-glucuronide that produces an insoluble precipitate having an approximately teal color when reacted upon by β-glucuronidase. Similarly, indoxyl-β-glucuronide is a similar compound, the preparation of which is described in the aforementioned article by Ley et al., in *Can J. Microbiol.*, the disclosure of which is incorporated by reference.

Another suitable β-galactoside is the compound 6-chloro-3-indolyl-β-D-galactoside which produces an insoluble precipitate having a pink/magenta color, the preparation of which is described in the aforementioned U.S. Pat. No. 5,210,022.

Other suitable compounds applicable as substrates in the practice of the present invention are specified in U.S. Pat. No. 5,210,022, all of which are incorporated herein by reference.

The substrate 8-hydroxyquinoline-β-D-glucuronide is a commercially available β-glucuronide that, in the presence of metallic ions such as iron, produces an insoluble precipitate having a substantially black color when reacted upon by β-glucuronidase and in the presence of other α- or β-galactoside substrates. 8-hydroxyquinoline-β-D-glucuronide is available from Biosynth International, Naperville, Ill.

Further, a salt providing ions suitable for use with the present invention is ferric ammonium citrate, available from Sigma Chemical, St. Louis, Mo. The cyclohexenoesculetin substrates are described in James et al., *Appl. & Envir. Micro.* 62:3868–3870 (1996) and in the presence of ferric ions, produce an insoluble substantially black precipitate.

N-methyl-indolyl substrates such as N-methylhydroxy-β-D-galactopyranoside are commercially available from Biosynth International, Naperville, Ill.

Nitrophenyl substrates, such as 2-nitrophenyl-β-D-galactopyranoside, are commercially available from Biosynth International, Naperville, Ill. Similarly, nitroaniline compounds are available for synthesis through Sigma Chemical, St. Louis, Mo.

Other substrates producing a substantially black color include esculetin substrates such as cyclohexenoesculetin-β-D-galactoside, which is described in James et al., *Appl. & Envir. Microbiol.* 62:3868–3870 (1996). Quinoline substrates, such as 8-hydroxyquinoline-β-D-galactopyranoside and 8-hydroxyquinoline-β-D-glucuronide are available through Biosynth International, Naperville, Ill.

Iodo-indolyl substrates, such as 5-iodo-3-indolyl-β-D-galactopyranoside are available through Biosynth International, Naperville, Ill.

Several fluorescent substrates are suitable for use with the present invention. Coumarin substrates such as 4-methylumbelliferyl substrates and 5-trifluoromethylumbelliferyl substrates are commercially available from Biosynth International, Naperville, Ill. Also suitable are fluorescein substrates, rhodamine substrates, and resorufin substrates. No commercial source is known for these three substrates but components are available from Sigma Chemical, St. Louis, Mo.

While specific examples of substrates suitable for use with the present invention have been enumerated hereinabove, such is not to be construed as limiting the invention in any manner. Instead, one of ordinary skill in the art can use Table IV and V hereinbelow to identify a virtually limitless number of substrates.

Preparation of Test Medium

The test medium is formed by combining the desired substrates with a nutrient base medium. The nutrient base medium can be any culture medium known in the art for providing the maintenance and reproduction of living cells. Generally, such media include nutrients, buffers, water, and sometimes a gelling agent. Possible gelling agents include agars, pectins, carrageenans, alginates, locust bean, and xanthins, among others.

The following is an example of the preparation of a test medium suitable for use in this invention. This example coincides with Example I, below.

The substrates 8-hydroxyquinoline-β-D-glucuronide, 5-Bromo-4-chloro-3-indolyl-α-D-galactopyranoside, and 6-Chloro-3-indolyl-β-D-galactopyranoside are added in quantities of 250 mg/L medium; 70 mg/L medium; and 175 mg/L medium, respectively. The substrates are added directly to the hot (75°–85° C.) medium (formula below) in a blender prior to sterilization.

Standard agar medium may be made by adding 15 gm of bacteriological quality agar gum to the following nutrient formula

| | |
|---|---|
| Pancreatic Digest of Casein | 5.0 gm |
| Yeast Extract | 3.0 gm |
| Dipotassium Phosphate | .3 gm |
| Deionized Water | 990 ml |
| Ferric Ammonium Citrate (sterilized separately from the other components) | 800 mg in 10 ml deionized water | and then sterilizing at 121° C. for 15 minutes. The medium should be adjusted to result in a pH of 7.0. The sterilized agar medium is allowed to drop to a temperature of 45° C. in a water bath and then the sterile solution containing the substrates prepared as described above is added. The medium is mixed thoroughly and poured into sterile petri plates at a volume of 20 ml/plate.

A pectin-based test medium may be prepared using the same steps described above except that 25 gm of low methoxyl pectin is used as the solidifying agent and the medium is poured at room temperature into petri plates containing a thin gel layer containing calcium ions which combine with the pectin to form a solid gel. A suitable pectin culture medium is described in U.S. Pat. Nos. 4,241,186 and 4,282,317, the disclosures of which are incorporated herein by reference. A pectin-based medium is preferred over a standard agar medium because it has the advantages of convenience and temperature independence for the user. The use of pectin media is well described and accepted as a result of AOAC collaborative studies and other published and in-house investigations.

A suitable pectin medium is commercially available from Micrology Laboratories, LLC under the trademark Easygel®. Aqueous based medium without gelling agent is available from Micrology Labs, Goshen Ind., for use with membrane filters.

Inoculation of the Test Medium with the Sample

The test medium may be inoculated with a sample to be tested for the presence of microorganisms by any method known in the art for inoculating a medium with a sample containing microorganisms. For example, the sample to be tested may be added to the petri plates prior to adding the nutrient base medium (pour plate technique) or spread on the surface of the plates after they have cooled and solidified (swab or streak plate technique). Liquid samples may also be filtered through a micropore (0.45 micrometer size) membrane filter which is then placed on the surface of a solid medium or on a pad saturated with the medium.

Incubation of the Test Medium

The inoculated test medium is incubated for a sufficient time and at such a temperature for individual microorganisms present in the sample to grow into detectable colonies. Suitable incubation conditions for growing microorganisms in a medium are known in the art. Commonly, the test medium is incubated for about 24–48 hours at a temperature of about 30°–40° C.

Unless inhibitors of the general microbial population are used, the general microbial population as well as general coliforms, $E.$ $coli$, Aeromonas spp., and Salmonella spp. and Shigella spp. will grow in the incubated test medium. Because the precipitates formed are insoluble in the test medium, they remain in the immediate vicinity of microorganisms producing the various enzymes. As the microorganisms reproduce to form colonies, the colonies show as colony forming units having the color produced by the particular substrate.

For example, $E.$ $coli$ produces $\beta$-galactosidase and $\alpha$-galactosidase, but, unlike general coliforms and Aeromonas spp., also produces $\beta$-glucuronidase. Therefore, insoluble precipitates of each of the $\beta$-galactosidase substrate, the $\alpha$-galactosidase substrate and the $\beta$-glucuronide substrate are formed by the action of the respective enzymes such that colonies of $E.$ $coli$ show as a substantially black color, sometimes having a violet-blue halo therearound.

General coliforms produce $\beta$-galactosidase and $\alpha$-galactosidase and consequently cleave both the $\alpha$-galactosidase and $\beta$-galactosidase substrates. In the present example, the 5-Bromo-4-chloro-3-indolyl-$\alpha$-D-galactoside substrate produces a blue-green or teal color, whereas the 6-Chloro-3-indolyl-$\beta$-D-galactoside produces a pink, or red-pink color. Thus, general coliform colonies will show as a blue-violet color, which is a combination of the colors produced by each of the $\alpha$- and $\beta$-galactosides, respectively.

Significantly, however, it has been found that Aeromonas spp., which are closely related to coliforms, and give an almost identical biochemical test pattern, are $\beta$-galactosidase positive and $\alpha$-galactosidase negative. That is, Aeromonas spp. will not hydrolize the $\alpha$-galactoside substrate. Therefore, Aeromonas colonies present in the test medium will show as colonies having the pink-red color produced by the $\beta$-galactoside substrate.

Further, it has been found that most members of the genera Salmonella and Shigella are positive for $\alpha$-galactosidase, but negative for $\beta$-galactosidase. That is, Salmonella and Shigella will not hydrolize the $\beta$-galactosidase substrate. Therefore, colonies of Salmonella and Shigella present in the test medium will appear as a teal, or blue-green color produced by the $\alpha$-galactoside substrate. Occasionally, Shigella colonies will appear black with a blue-green halo since some strains of Shigella are positive for $\beta$-glucuronidase, and some strains of Shigella will appear blue/purple since some unusual strains are positive for both $\alpha$-galactosidase and $\beta$-galactosidase.

Examination of the Test Medium and Enumeration of Microorganisms

The substrates selected for the above example produce three distinct colors, and general coliforms are indicated by a fourth color which is a combination of two of the three colors. That is, $E.$ $coli$ colonies show as substantially black, general coliform colonies show as blue-violet, Aeromonas colonies show as red-pink, and Salmonella and Shigella colonies show as teal-green. While the individual shades of these colors may vary somewhat in the test medium due to factors such as varying enzyme production of the biological entities, it has been found that these four colors are distinct enough so that confusion amongst them is unlikely.

The colonies of each type of microorganism may be enumerated by counting the colonies or by other methods known in the art for enumerating microorganisms on a test plate. The number of colonies of each type indicates the number of microorganisms of each type originally present in the sample before incubation.

Optional Ingredients

Inhibitors

The method of the present invention does not require inhibitors. However, the medium may be made more selective for general coliforms and $E.$ $coli$ if desired by the addition of various compounds that are inhibitory to the general microbial population, but have little or no effect on coliforms. Following are some compounds which may be used: a) bile salts, about 0.3 g/liter, b) sodium lauryl sulfate, about 0.2 g/liter, c) sodium desoxycholate, about 0.2 g/liter, d) Tergitol 7, about 0.1 ml/liter. The use of one or more of these compounds reduces the background (non-coliform) microorganism presence and makes a less cluttered plate and eliminates the possibility of inhibition or interference by the non-coliform organisms in the sample. The use of certain antibiotics may accomplish the same result.

Cefsulodin is commonly used in currently available test media to inhibit Aeromonas spp. However, the use of cefsulodin as an inhibitor requires an extra step in the process, viz., sterile addition of filter sterilized antibiotic. This step is difficult to control. Further, the presence of cefsulodin significantly reduces the effective shelf life of the medium. It has been found that Nalidixic acid can be used instead of Cefsulodin to inhibit Aeromonas spp. with about the same efficacy. Nalidixic acid is preferable because it can survive the approximately 120° C. temperature reached in autoclaving the test media. Therefore, unlike cefsulodin, nalidixic acid can be added to the test media as part of the initial media formulation prior to sterilization (see, preparation of test medium, above). It also follows that the resistance of the nalidixic acid to unfavorable environmental conditions will result in a longer shelf life for a medium containing it as compared to cefsulodin.

Inducers

It is possible that the enzyme production of the general coliforms may be enhanced by the addition to the medium formulations of very small amounts of substances known as enzyme inducers. One specific inducer for $\beta$-galactosidase is available and is known chemically as isopropyl-$\beta$-thiogalactopyranoside. Adding approximately 100 mg/liter of medium has a positive and noticeable effect on the speed of enzyme production for some species of coliforms. Other enzyme inducers are available and may be added to media formulations if enhanced enzyme production is deemed helpful.

EXAMPLES

Listed below are broad examples of test media enzyme substrate combinations to be used in combination with the nutrient formula discussed above or other suitable nutrient formulas which may be prepared in practicing the present invention.

Table III illustrates the flexibility of the preferred embodiments incorporating the present invention. Table III is a matrix of some of the possible four-color combinations available for the preferred biological entities *E. coli,* general coliforms, and at least one of the genera Aeromonas, Salmonella or Shigella to be detected by using the teachings of this disclosure. Other color combinations are possible. In many cases, a plurality of different substrates will achieve a desired result, the only difference being the colors detected for a specific enzyme. The preferred color choice for the detection of *E. coli* is denoted with an asterisk in Table III, depending on the colors chosen to detect other microorganisms. As discussed above, the substantially black color is preferred because other chromogenic substrates do not interfere with it and the substantially black color is easy to distinguish from the other colors.

As discussed above, the use of Table III requires taking into account the combined color effect discussed above which is produced by the inclusion of multiple chromogenic substrates in a single medium. For example, with reference to the first entry in Table III, it can be understood that general coliforms will appear as a combination of (1) red-pink (magenta) and (2) teal, the resulting color being blue-violet. This is the case because general coliforms are responsive to two chromogenic substrates. Similarly, general coliforms will show in a test medium in accordance with the second entry of Table III as a combination of (1) red-pink (magenta) and (2) yellow.

TABLE III

Color possibilities for detection of preferred microorganisms

| desired color→ | red-pink or mageneta | teal | green | yellow | black | fluorescent | fluorescent | fluorescent |
|---|---|---|---|---|---|---|---|---|
| 1 | general coliforms Aeromonas | general coliforms Salmonella/shigella | *E. coli* | *E. coli* | *E. coli** | *E. coli* | | |
| 2 | general coliforms Aeromonas | *E. coli* | *E. coli* | general coliforms Salmonella/shigella | *E. coli** | *E. coli* | | |
| 3 | *E. coli* | general coliforms Aeromonas | *E. coli* | general coliforms Salmonella/shigella | *E. coli** | *E. coli* | | |
| 4 | general coliforms Salmonella/shigella | *E. coli* | general coliforms Aeromonas | *E. coli* | *E. coli** | *E. coli* | | |
| 5 | *E. coli* | general coliforms Salmonella/shigella | general coliforms Aeromonas | *E. coli* | *E. coli** | *E. coli* | | |
| 6 | *E. coli* | *E. coli* | general coliforms Aeromonas | general coliforms Salmonella/shigella | *E. coli** | *E. coli* | | |
| 7 | *E. coli* | *E. coli* | *E. coli* | *E. coli* | general coliforms Aeromonas | general coliforms Salmonella/shigella | *E. coli* | |
| 8 | general coliforms Aeromonas | *E. coli* | *E. coli* | *E. coli* | *E. coli** | general coliforms Salmonella/shigella | *E. coli* | |
| 9 | *E. coli* | general coliforms Aeromonas | *E. coli* | *E. coli* | *E. coli** | general coliforms Salmonella/shigella | *E. coli* | |
| 10 | *E. coli* | *E. coli* | general coliforms Aeromonas | *E. coli* | *E. coli** | general coliforms Salmonella/shigella | *E. coli* | |
| 11 | *E. coli* | *E. coli* | *E. coli* | general coliforms Aeromonas | *E. coli** | general coliforms Salmonella/shigella | *E. coli* | |
| 12 | general coliforms Aeromonas | *E. coli* | *E. coli* | *E. coli* | general coliforms Salmonella/shigella | *E. coli* | | |
| 13 | *E. coli* | general coliforms Aeromonas | *E. coli* | *E. coli* | general coliforms Salmonella/shigella | *E. coli* | | |
| 14 | *E. coli* | *E. coli* | general coliforms Aeromonas | *E. coli* | general coliforms Salmonella/shigella | *E. coli* | | |

TABLE III-continued

Color possibilities for detection of preferred microorganisms

| desired color | red-pink or magenta | teal | green | yellow | black | fluorescent | fluorescent | fluorescent |
|---|---|---|---|---|---|---|---|---|
| 15 | E. coli | E. coli | E. coli | general coliforms Aeromonas | general coliforms Salmonella/shigella | E. coli | | |
| 16 | E. coli | E. coli | E. coli | E. coli | E. coli* | E. coli | general coliforms Aeromonaceae monas | general coliforms Salmonella/shigella |

*= preferred color for E. coli

Table IV is a partial list of enzyme patterns for biological entities preferred to be to be detected in accordance with the teachings of this disclosure. It is to be understood that one of ordinary skill in the art would readily recognized that other enzymes which are known and have been produced, and enzymes which are known only on a theoretically level, would also perform satisfactorily.

listed on the right hand side of table V can be combined with any of the chromogenic or nonchromogenic components listed on the left hand side of table V to identify a specific substrate for use in a test medium. It can therefore be understood that Table V teaches a large quantity of substrates possible for use in accordance with the present invention. Many of the substrates identified by the above-

TABLE IV

| ENZYME NAME | E. coli | GENERAL COLIFORM | Aeromonas | Salmonella/ Shigella | Plesiomonas | Vibrio |
|---|---|---|---|---|---|---|
| Aara = α-D-arabinopyranosidase | + | + | − | + | | |
| Agal = α-D-galactopyranosidase | + | + | − | + | | |
| Aglu = α-D-glucopyranosidase | − | + | + | − | + | |
| Bcel = β-D-cellopyranosidase | − | + | − | − | − | − |
| Bfuc = β-D-fucopyranosidase | + | + | + | − | − | − |
| Bgal = β-D-galactopyranosidase | + | + | + | − | + | + |
| Bgal = β-D-glucopyranosidase | + | + | + | − | − | − |
| Bgluc = β-D-glucuronidase | + | − | − | − | − | − |
| Bman = β-D-mannopyranosidase | + | + | − | + | + | + |
| Bxyl = βD-xylopyranosidase | − | + | − | − | | |
| Nagal = N-acetyl-β-D-galactopyranosidase | − | + | + | − | + | + |
| Naglu = N-acetyl-β-D-glucopyranosidase | − | + | + | − | + | + |
| Aman = α-D-mannopyranosidase | − | − | − | − | − | − |
| esterase = esterase | − | − | − | + | − | − |

Table V is a matrix which teaches a wide variety of substrates and their associated colors for use in test media in accordance with the teachings of this disclosure. The left hand side of Table V indicates the color that will result when the listed chromogenic component is cleaved from its corresponding substrate by the specific enzyme for that substrate. In the case of the nonchromogenic components, the color is substantially black and the reaction mechanism requires the presence of ions of a salt upon cleavage of the substrate, as explained above.

Test enzymes which are produced by certain biological entities (see Table IV) are found at the right hand side of table V. "Substrate components" are shown to the left of the specific test enzymes. Each of the substrate components described use of table V are commercially available, whereas the method for producing other identified substrates is described in the literature. Still other substrates identified by using table V are only theoretically possible.

Nonchromogenic components are included at the bottom left hand side of Table V, and are different from the chromogenic components because they do not form specific colors upon cleavage. Instead, the quinoline or esculetin components combine with ions of a salt (e.g., ferric salt) which must be present in the medium when the substrate is cleaved by the specific enzyme. The substantially black precipitate formed by the nonchromogenic components is a combination of the quinoline or esculetin—iron complex rather than a dimer which is formed by the chromogenic components.

Unlike nonchromogenic components, the chromogenic components should be selected in view of all other chromogenic components selected for the medium and in view of the enzyme patterns of the entities to be detected. The selection of chromogenic components should maximize the distinction among the respective colors produced.

While many various chromogenic component and substrate component/enzyme possibilities are taught by Table V, other possibilities within the scope of the appended claims would be possible by one of ordinary skill in the art. For example, as shown in Table V, one of ordinary skill in the art could combine an N-acetyl group with many of the sugars of the substrate components listed in Table V. For example, an N-acetyl group could be combined with β-D-mannopyranoside to form N-acetyl-β-D-mannosaminide, the corresponding enzyme being N-acetyl-β-D-mannosaminidase. Any of the chromogenic components or nonchromogenic components listed on the left hand side of Table V could then be combined with the substrate component to identify a substrate. If the substrate is commercially available or the method of making it is known, the substrate could be used in a test medium. Upon cleavage of the substrate by the corresponding enzyme in the test medium, the color listed will appear.

Generally, the teachings of this disclosure can be used as follows to make a test medium for detecting various microorganisms or cell types. First, the microorganisms desired to be detected and differentiated are selected. The preferred organisms to be detected are *E. coli,* general coliforms, and at least one of the genera Aeromonas, Salmonella or Shigella. Enzymes produced by the selected organisms can be identified with reference to Table IV. Equipped with knowledge of specific enzymes produced by each microorganism, one can then identify corresponding substrates components from the right hand side of Table V. Depending upon the color desired, one can select a chromogenic or nonchromogenic component from Table V to be combined with the substrate component to identify a substrate for inclusion in the test medium. If the substrate thereby identified is commercially available or the method of its synthesis is known, the substrate can be used in the test medium.

TABLE V

COLOR COMPONENT AND SUBSTRATE COMPONENT MATRIX

| CHROMOGENIC COMPONENT & | (COLOR) |
|---|---|
| 6-fluoro-3-indolyl- | (pink) |
| 6-chloro-3-indolyl- | (pink/red) |
| 5-bromo-6-chloro-3-indolyl- | (magenta) |
| 3-indolyl- | (teal) |
| 5-bromo-4-chloro-3-indolyl- | (teal) |
| 5-iodo-3-iondolyl- | (purple) |
| N-methylindolyl- | (green) |
| 4-methylumbelliferyl- | (fluorescent) |
| rhodamine- | (fluorescent) |
| fluorescein- | (fluorescent) |
| resorufin- | (fluorescent) |
| coumarin | (fluorescent) |
| nitrophenyl- | (yellow) |
| nitroaniline | (yellow) |

| NONCHROMOGENIC COMPONENT | (COLOR) |
|---|---|
| 8-hydroxyquinoline plus ions- | (substantially black) |
| 3,4-cyclohexenoesculetin plus ions | (substantially black) |
| esculetin plus ions- | (substantially black) |

SUBSTRATE COMPONENT - - TEST ENZYME

α-D-arabinopyranoside -- Aara.
α-D-cellopyranoside -- Acel.
α-D-fucopyranoside -- Afuc.
α-D-galactopyranoside -- Agal.
α-D-glucuronide -- Agluc.
α-D-mannopyranoside -- Aman.
α-D-xylopyranoside -- Axyl.
β-D-arabinopyranoside -- Bara.
β-D-cellopyranoside -- Bcel.
β-D-fucopyranoside -- Bfuc.
β-D-galactopyranoside -- Bgal.
β-D-glucopyranoside -- Bglu.
β-D-glucuronide -- Bgluc.
β-D-mannopyranoside -- Bman.
β-D-xylopranoside -- Bxyl.
N-acetyl-β-D-galactosaminide -- Nagal
N-acetyl-β-D-glucosaminide -- Naglu
N-acetyl-β-D-glucuronaminide -- Nagluc
N-acetyl + other sugar components
butyrate -- esterase
caprylate -- esterase
palmitate -- esterase Tavle VI is a concise summary of the specific examples.

TABLE VI

EXAMPLE SUMMARIES

| Example # | Substrate | *E. coli* | General Coliforms | Aeromonas | Salmonella/ Shigella |
|---|---|---|---|---|---|
| I | 8-hydroxyquinoline-β-D-glucuronide | X | | | |
| | 6-chloro-3-indolyl-β-D-galactopyranoside | X | X | X | |
| | 5-bromo-4-chloro-3-indolyl-α-D-galactopyranoside | X | X | | X |
| | color→ | Black | Purple-Blue | Pink | Teal |
| II | 8-hydroxyquinoline-β-D-glucuronide | X | | | |
| | 6-chloro-3-indolyl-β-D-galactopyranoside | X | X | X | |
| | 6-chloro-3-indolyl-β-D-mannoside | X | X | | X |
| | 5-bromo-4-chloro-3-indolyl-α-D-galactopyranoside | X | X | | X |
| | color→ | Black | Purple-blue | Red-pink | Purple-blue |

TABLE VI-continued

EXAMPLE SUMMARIES

| Example # | Substrate | E. coli | General Coliforms | Aeromonas | Salmonella/Shigella |
|---|---|---|---|---|---|
| IIIA | 8-hydroxyquinoline-β-D-glucuronide | X | | | |
| | 6-chloro-3-indolyl-β-D-galactopyranoside | X | X | X | |
| | 6-chloro-3-indolyl-α-D-galactopyranoside | X | X | | X |
| | 5-bromo-4-chloro-3-indolyl-β-D-galactopyranoside | X | X | X | |
| | color→ | Black | Purple-blue | Purple-blue | Pink |
| IIIB | 8-hydroxyquinoline-β-D-glucuronide | X | | | |
| | 6-chloro-3-indolyl-β-D-galactopyranoside | X | X | X | |
| | 5-bromo-4-chloro-3-indolyl-α-D-galactopyranoside | X | X | | X |
| | 5-bromo-4-chloro-3-indolyl-β-D-galactopyranoside | X | X | X | |
| | color→ | Black | Purple-blue | Purple-blue | Teal |
| IIIC | May eliminate Aeromonas with inhibitors which allows removal of 6-chloro-3-indolyl-β-D-galactopyranoside from Examples IIIA and IIIB | | | | |
| IV | 6-chloro-3-indolyl-β-D-galactopyranoside | X | X | X | |
| | 6-chloro-3-indolyl-β-D-mannoside | X | X | | X |
| | 5-bromo-4-chloro-3-indolyl-α-D-galactopyranoside | X | X | | X |
| | color→ | Purple-Blue | Purple-blue | Pink | Purple-blue |
| V-A | 6-chloro-3-indolyl-β-D-galactopyranoside | X | X | X | |
| | 6-chloro-3-indolyl-α-D-galactopyranoside | X | X | | X |
| | 5-bromo-4-chloro-3-indolyl-β-D-galactopyranoside | X | X | X | |
| | color→ | Purple-blue | Purple-blue | Purple-blue | Pink |
| V-B | 6-chloro-3-indolyl-β-D-galactopyranoside | X | X | X | |
| | 5-bromo-4-chloro-3-indolyl-α-D-galactopyranoside | X | X | | X |
| | 5-bromo-4-chloro-3-indolyl-β-D-galactopyranoside | X | X | X | |
| | color→ | Purple-blue | Purple-blue | Purple-blue | Teal |
| V-C | May eliminate Aeromonas with inhibitors which allows removal of substrate No. 1 from example V-A and allows removal of substrate No. 3 from example V-B | | | | |
| VI | 5-bromo-4-chloro-3-indolyl-α-D-galactopyranoside | X | X | | X |
| | 6-chloro-3-indolyl-β-D-galactopyranoside | X | X | X | |
| | color→ | Purple-blue | Purple-blue | Pink | Teal |
| VII | 8-hydroxyquinoline-β-D-glucuronide | X | | | |
| | 5-bromo-4-chloro-3-indolyl-α-D-galactopyranoside | X | X | | X |
| | 6-chloro-3-indolyl-N-acetyl-β-D-galactosaminide | | X | X | |
| | color→ | Black | Purple-blue | Pink (see note) | Teal |
| | Note: In example 7, Vibrio and Plesiomonas also show as pink along with Aeromonas | | | | |
| VIII | 8-hydroxyquinoline-β-D-glucuronide | X | | | |
| | 5-bromo-4-chloro-3-indolyl-α-D-galactopyranoside | X | X | | X |
| | 6-chloro-3-indolyl-β-D-mannoside | X | X | | X |
| | 6-chloro-3-indolyl-N-acetyl-β-D-galactosaminide | | X | X | |
| | color→ | Black | Purple-blue | Pink (see note) | Purple-blue |
| | Note: In example 8, Vibrio and Plesiomonas also show as pink along with Aeromonas | | | | |
| IX | 5-bromo-4-chloro-3-indolyl-α-D-galactopyranoside | X | X | | X |
| | 6-chloro-3-indolyl-β-D-galactopyranoside | X | X | X | |
| | 6-chloro-3-indolyl-N-acetyl-β-D-galactosaminide | | X | X | |
| | color→ | Purple-blue | Purple-blue | Pink | Teal |
| X | 6-chloro-3-indolyl-N-acetyl-β-D-galactosaminide | | X | X | |
| | 5-bromo-4-chloro-3-indolyl-α-D-galactopyranoside | X | X | | X |
| | 6-chloro-3-indolyl-β-D-galactopyranoside | X | X | X | |
| | color→ | Purple-blue | Purple-blue | Pink (see note) | Teal |
| | Note: For example 10, Vibrio and Plesiomonas also show as pink along with Aeromonas | | | | |
| XI | 8-hydroxyquinoline-β-D-glucuronide | X | | | |
| | 6-chloro-3-indolyl-β-D-galactopyranoside (or) | X | X | X | |
| | 5-bromo-6-chloro-3-indolyl-β-D-galactopyranoside | X | X | X | |
| | color→ | Black | Pink or Teal | Pink or Teal | Not detected |
| | Note: In example 11, Aeromonas may be eliminated by adding inhibitors | | | | |
| XII | 8-hydroxyquinoline-β-D-galactopyranoside | X | X | X | |
| | 5-bromo-4-chloro-3-indolyl-α-D-galactopyranoside (or) | X | X | | X |

TABLE VI-continued

EXAMPLE SUMMARIES

| Example # | Substrate | E. coli | General Coliforms | Aeromonas | Salmonella/ Shigella |
|---|---|---|---|---|---|
| | 6-chloro-3-indolyl-α-D-galactopyranoside color→ Note: In example 13, Aeromonas may be eliminated by adding an inhibitor | X Black | X Black | Black | X Teal or Pink |
| XIII | Use same substrates as in example No. 1, and add: 4-methyl-umbelliferyl-β-D-xylopyranoside | Enterobacter and Klebsiella showing as black colonies will fluoresce, thereby allowing reduction in false positive count of E. coli. | | | |
| XIV | 8-hydroxy-quinoline-β-D-glucuronide 6-chloro-3-indolyl-caprylate color→ | X Black | | | X Red-pink |
| XV | 8-hydroxy-quinoline-β-D-glucuronide 5-bromo-4-chloro-3-indolyl-caprylate 6-chloro-3-indolyl-α-D-galactopyranoside color→ | X X Black | X Red-pink | | X X Blue-violet |
| XVI | 8-hydroxy-quinoline-β-D-glucuronide 5-bromo-4-chloro-3-indolyl-β-D-galactopyranoside (or) 5-bromo-6-chloro-3-indolyl-β-D-galactopyranoside color→ | X X X Black | X X Teal (or) Magenta | Inhibitor present | |

Example I

The microorganisms chosen to be identified, quantified and differentiated are E. coli, general coliforms, Aeromonas, Shigella or Salmonella.

With reference to Table IV, E. coli produces the enzyme Bgluc, and Bgluc is not produced by any of the other microorganisms desired to be detected. With reference to the right hand side of Table V, it can be seen that the test enzyme Bgluc has a corresponding substrate component of β-D-glucuronide. Thus, a chromogenic or nonchromogenic component which produces a distinct color upon cleavage of Bgluc should be chosen from the left hand side of Table V. 8-hydroxyquinoline is chosen for its preferred substantially black color. The first identified substrate is therefore 8-hydroxyquinoline-β-D-glucuronide, the availability of which is described above. A metallic salt such as ferric ammonium citrate is also required and is added to the test medium so that, upon cleavage of the substrate by Bgluc, a substantially black water-insoluble complex forms in the medium. The substantially black precipitate consists of the ferric ions and the aglycone released when the substrate is hydrolyzed by the glucuronidase from E. coli.

With firther reference to Table IV, Bgal, Bfuc and Bglu are common to Aeromonas and general coliforms. However, as indicated in Table IV, Bgal, Bfuc and Bglu are not produced generally by Salmonella and Shigella. Therefore, a substrate component corresponding to one of Bgal, Bfuc and Bglu can be selected form the right hand side of Table V. Bgal and the associated substrate component β-D-galactopyranoside are chosen. The 6-chloro-3-indolyl-chromogenic component produces a red-pink color upon cleavage from its substrate in the presence of Bgal and is selected as the chromogenic component. The second substrate is therefore 6-chloro-3-indolyl-β-D-galactopyranoside.

Again referring to Table IV, Bman, Aara and Agal are common to Salmonella, Shigella and general coliforms. However, as indicated in Table IV, Bman, Aara and Agal are not produced by Aeromonas. Thus, one of Bman, Aara and Agal can be chosen and its associated substrate component identified with reference to Table V. The test enzyme Agal and the respective substrate component α-D-galactopyranoside are chosen. Next, a chromogenic component must be selected from Table V. As shown on the left hand side of Table V, the chromogenic component 5-bromo-4-chloro-3-indolyl produces a teal color upon cleavage from its associated substrate and is therefore selected. The third substrate is therefore 5-bromo4-chloro-3-indolyl-α-D-galactopyranoside.

General coliforms have a wide enzyme pattern which is responsive to both the 6-chloro-3-indolyl-β-D-galactopyranoside substrate and the 5-bromo-4-chloro-3-indolyl-α-D-galactopyranoside substrate. Therefore, general coliforms will show as a fourth distinct color which is a combination of the colors produced by the two aforementioned substrates, respectively. In this case the fourth color will be violet-blue, which is a combination of red-pink and teal.

Finally, as seen in Table IV, E. coli also exhibits a wide enzyme pattern and responsive to all three of the substrates chosen in this example, viz., 8-hydroxyquinoline-β-D-glucuronide, 6-chloro-3-indolyl-β-D-galactopyranoside, and 5-bromo-4-chloro-3-indolyl-α-D-galactopyranoside. Nonetheless, E. coli colonies present in the test medium will show as a substantially black color because, as discussed above, the chromogenic substrates do not interfere with the substantially black color. Advantageously, this substantially black color provides a superior means for distinguishing the E. coli, as well as allows four separate microorganisms to be detected, quantified, differentiated and identified in a single test medium. See Table VI.

Example II

The selected microorganisms to be detected, quantified, differentiated and identified are E. coli as a first color; general coliforms, Salmonella and Shigella as a second color; and Aeromonas as a third color.

With reference to Table IV, E. coli produces the enzyme Bgluc, and Bgluc is not produced by any of the other microorganisms desired to be detected. With reference to the right hand side of Table V, it can be seen that the test enzyme Bgluc has a corresponding substrate component of β-D-glucuronide. Thus, a chromogenic or nonchromogenic component which produces a distinct color upon cleavage of Bgluc should be chosen from the left hand side of Table V. 8-hydroxyquinoline is chosen for its preferred substantially black color. The first identified substrate is therefore 8-hydroxyquinoline-β-D-glucuronide, the availability of which is described above. A metallic salt such as ferric ammonium citrate is also required and is added to the test medium so that, upon cleavage of the substrate by Bgluc, a substantially black water-insoluble complex forms in the medium. The substantially black precipitate consists of the ferric ions and the aglycone released when the substrate is hydrolized by the glucuronidase from E. coli.

With further reference to Table IV, Bgal, Bfuc and Bglu are common to Aeromonas and general coliforms. However, as indicated in Table IV, Bgal, Bfuc and Bglu are not produced by Salmonella or Shigella. Using Table V in the fashion described above, 6-Chloro-3-indolyl-β-D-galactopyranoside is selected as the second substrate, which will produce a red-pink color upon cleavage as indicated by the chromogenic component list of Table V.

As seen in Table IV, the enzyme Bman is common to Salmonella/Shigella but not Aeromonas. From table V, the substrate component associated with Bman is β-D-mannopyranoside. In this example, it is desired to also produce the second distinct color (red-pink) with Salmonella/Shigella so that, ultimately, Salmonella/Shigella colonies present in the test medium will show as the same color as general coliforms present in the test medium Thus, the chromogenic component is 6-Chloro-3-indolyl- and the third substrate is therefore 6-Chloro-3-indolyl-β-D-mannopyranoside.

In this example, again using Table V, a fourth substrate is identified that will be cleaved by one of the enzymes Bman, Aara, Agal common to Salmonella/Shigella to produce a third distinct color. Using table V in the fashion described above, the fourth substrate selected is 5-Bromo4-chloro-3-indolyl-α-D-galactopyranoside, which produces a teal-green color in the presence of Agal common to Salmonella/Shigella.

The resulting colors of colonies present in the test medium can be predicted as follows. E. coli exhibits a wide enzyme pattern that is positive for all four of the substrates chosen in this example, including the 8-hydroxy-glucuronide substrate which produces a substantially black color upon cleavage in the presence of the ions of the ferric salt. E. coli colonies show as substantially black. Aeromonas has an enzyme pattern which reacts with only the 6-Chloro-3-indolyl-β-D-galactopyranoside substrate chosen in this example and therefore colonies of Aeromonas show as red-pink. Salmonella/Shigella has an enzyme pattern which cleaves both the third and fourth substrates selected in this example and therefore colonies of Salmonella/Shigella show as purple-blue (a combination of teal and red-pink). Finally, general coliforms are positive for each of the second, third and fourth substrates selected and colonies thereof show as purple-blue, indistinguishable from the Salmonella/Shigella colonies. As discussed above, different strains of all species of the various genera will not all produce the same amounts of the various enzymes, so there may be slight variations in shades of purple-blue, for example.

Example IIIA

The selected microorganisms to be quantified and differentiated in this example are E. coli as a first color, general coliforms and Aeromonas as a second color, and Salmonella/Shigella as a third color.

With reference to Table IV, E. coli produces the enzyme Bgluc, and Bgluc is not produced by any of the other microorganisms desired to be detected. With reference to the right hand side of Table V, it can be seen that the test enzyme Bgluc has a corresponding substrate component of β-D-glucuronide. Thus, a chromogenic or nonchromogenic component which produces a distinct color upon cleavage of Bgluc should be chosen from the left hand side of Table V. 8-hydroxyquinoline is chosen for its preferred substantially black color. The first identified substrate is therefore 8-hydroxyquinoline-β-D-glucuronide, the availability of which is described above. A metallic salt such as ferric ammonium citrate is also required and is added to the test medium so that, upon cleavage of the substrate by Bgluc, a substantially black water-insoluble complex forms in the medium. The substantially black precipitate consists of the ferric ions and the aglycone released when the substrate is hydrolized by the glucuronidase from E. coli.

Using tables IV and V in a fashion similar to that described above with reference to Examples I and II, 6-Chloro-3-indolyl-β-D-galactopyranoside is selected as a second substrate to combine with one of the enzymes Bgal, Bfuc and Bglu common to coliforms and Aeromonas, but negative for Salmonella/Shigella to produce a second distinct color, in this case substantially red-pink.

Similarly, 6-Chloro-3-indolyl-α-D-galactopyranoside is selected as a third substrate to combine with Agal, which is common to coliforms and Salmonella/Shigella, but negative for Aeromonas. Upon reaction with the enzyme, this substrate will also produce the same distinct second color, namely red-pink.

5-Bromo-4-chloro-3-indolyl-β-D-galactopyranoside is selected as a fourth substrate to combine with the enzyme Bgal, which is common to coliforms and Aeromonas, but negative for Salmonella/Shigella. This fourth substrate produces a teal-green color upon reaction with Bgal.

The resulting colors of colonies present in the test medium can be predicted as follows. E. coli exhibits a wide enzyme pattern and is positive for all four of the substrates chosen in this example. Therefore, E. coli colonies will show as substantially black. General coliform colonies have an enzyme pattern which is positive for the second, third and fourth substrates, so that general coliforms colonies show as purple-blue. Aeromonas colonies have an enzyme pattern which is positive for the second and fourth substrates chosen so that Aeromonas colonies also show as purple-blue. Finally, the enzymes common to Salmonella/Shigella are only positive for the third of the four substrates, so that Salmonella/Shigella colonies show as red-pink.

Example IIIB

As a variation, the test medium of Example IIIA can be prepared such that colonies of Salmonella/Shigella will show as teal instead of pink-red, all of the other colony colors being the same as Example IIIA. With reference to Table VI, such can be accomplished by replacing the 6-chloro-3-indolyl-α-D-galactopyranoside of Example IIIA with 5-bromo-4-chloro-3-indolyl-α-D-galactopyranoside.

Example IIIC

A second, independent method for producing the same three colors as Example IIIA for the same four components can be achieved by adding nalidixic acid or other antibiotics or inhibitors of Aeromonas to the components listed in Example 1. In so doing, the cefsulodin or nalidixic acid or other substance acts as an inhibitor for Aeromonas so Aeromonas colonies do not grow. If Aeromonas is eliminated, then the purple-blue colonies are all true coliforms. If not eliminated, any Aeromonas will be counted as part of the coliforms which some persons may prefer since Aeromonas is an important indicator organism.

Example IV

In this example, the selected microorganisms to be detected, quantified and differentiated are E. coli, coliforms and Salmonella/Shigella as a first distinct color and Aeromonas as a second distinct color. One test medium which achieves this result is the test medium described in Example II, except that the first substrate and metallic salt are omitted. Thus, because the enzyme pattern of E. coli reacts with the same substrates as the enzyme pattern for general coliforms, E. coli and general coliforms will be the same color in this test medium. Specifically, E. coli, coliforms and Salmonella/Shigella colonies will show as a purple-blue color, whereas Aeromonas colonies will show as a substantially red-pink color.

Example V

The selected microorganisms to be detected, quantified and differentiated are E. coli, general coliforms and Aeromonas as a first distinct color, and Salmonella/Shigella as a second distinct color. One test medium which achieves this result is the test medium of Example 3 with the first substrate and metallic salt being omitted. In this test medium, E. coli, general coliforms and Aeromonas colonies will show as a generally purple-blue color, whereas Salmonella and Shigella colonies will show as a generally teal-green color or as a red-pink color.

Optionally, the 6-chloro-3-indolyl-α-D-galactoside can be replaced with 5-bromo-4-chloro-3-indolyl-β-D-galactoside so that Salmonella colonies show as teal, rather than pink.

A third way to achieve the same result is with an antibiotic, preferably nalidixic acid, to inhibit the growth of Aeromonas colonies. If Aeromonas is eliminated, then the purple-blue colonies are all true coliforms. If not eliminated, any Aeromonas will be counted as part of the coliforms which some persons may prefer since Aeromonas is an important indicator organism.

Example VI

The selected microorganisms to be detected, quantified and differentiated are E. coli and coliforms as a first distinct color, Aeromonas as a second distinct color and Salmonella/Shigella as a third distinct color. A test medium which achieves this result is the test medium of Example I with the first substrate and metallic salt being omitted. In such a test medium, E. coli and general coliform colonies will show as purple-blue, Aeromonas colonies will show as generally red-pink, and Salmonella or Shigella colonies will show as generally teal-green.

Example VII

The selected microorganisms to be detected, quantified and differentiated are E. coli as a first distinct color which is substantially black; general coliforms as a second distinct color which is substantially purple-blue; Aeromonas/Vibrio/Plesiomonas as a third distinct color which is substantially red-pink; and Salmonella or Shigella as a fourth distinct color which is substantially teal-green.

With reference to Table IV, E. coli produces the enzyme Bgluc, and Bgluc is not produced by any of the other microorganisms desired to be detected. Therefore, a substrate which produces a distinct color upon cleavage of Bgluc should be chosen from Table V. 8-hydroxyquinoline-β-D-glucuronide produces a substantially black color in the presence of Bgluc and would be the preferred choice of substrate, as explained below. A metallic salt such as ferric ammonium citrate is also added to form a substantially black water insoluble complex consisting of the ferric ions and the aglycone released when the substrate is hydrolyzed by the glucuronidase from E. coli.

With further reference to Table IV, it can be seen that the enzyme Ngal and Naglu are common to the microorganisms Aeromonas, Plesiomonas, and Vibrios. Therefore, a suitable substrate for testing all of these microorganisms as a single distinct color is 6-chloro-3-indolyl-N-acetyl-β-D-galactosaminide, which produces a substantially red-pink color in the presence of these enzymes.

Again referring to Table IV, Bman, Aara and Agal are common to Salmonella/Shigella and general coliforms. However, as indicated in Table IV, Bman, Aara and Agal are not produced by Aeromonas. Therefore, a substrate can be selected from Table V which reacts with one of Bman, Aara and Agal to produce a third distinct color. As shown in Table V, 5-bromo-4-chloro-3-indolyl-α-D-galactoside produces a teal-green color in the presence of Agal and is therefore selected as a substrate.

In this test medium E. coli colonies will show as substantially black, general coliform colonies will show as substantially purple-blue, Aeromonas, Vibrio and Plesiomonas colonies will show as substantially red-pink, and Salmonella or Shigella colonies will show as substantially teal.

Example VIII

The selected microorganisms to be detected, quantified and differentiated are E. coli as a first distinct color; coliforms, Salmonella or Shigella as a second distinct color; and Aeromonas, Virbrio and Plesiomonas as a third distinct color. One test medium for achieving this result is the test medium of Example 2, except that the fourth substrate chosen is 6-Chloro-3-indolyl-N-acetyl-α-D-galactosaminide, to which each of the microorganisms Plesiomonas, Vibrios and Aeromonas are responsive so that each of these colonies shows as a generally red-pink color.

Example IX

The selected microorganisms to be detected, quantified and differentiated in this example are E. coli and general coliforms as a first distinct color which is purple-blue; Aeromonas, Plesiomonas, and Vibrios as a second distinct color which is red-pink; and Salmonella or Shigella as a third distinct color which is teal-green. This result can be achieved with the test medium as described in Example 6 with the addition of 6-Chloro-3-indolyl-N-acetyl-β-D-galactosaminide, to which each of the microorganisms Plesiomonas, Vibrio and Aeromonas is responsive.

Example X

The selected microorganisms to be detected, quantified and differentiated in this example are E. coli and general coliforms as a first color; Aeromonas, Vibrio and Plesiomonas as a second distinct color; and Salmonella or Shigella as a third distinct color. A suitable test medium that achieves this result is the test medium disclosed in Example 7 except that the first substrate for detecting *E. coli* colonies is omitted. In this example, *E. coli* and general coliform colonies show as generally purple-blue, Aeromonas, Vibrio and Plesiomonas show as generally red-pink, and Salmonella or Shigella show as generally teal-green. The addition of 6-Chloro-3-indolyl-β-D-galactopyranoside is necessary to yield the purple-blue color for *E. coli* colonies.

Example XI

The selected microorganisms to be detected, quantified and differentiated in this example are *E. coli* as a substantially black color and general coliforms as a red-pink color.

With reference to Table IV, *E. coli* produces the enzyme Bgluc, and Bgluc is not produced by any of the other microorganisms desired to be detected. Therefore, a substrate which produces a distinct color upon cleavage of Bgluc should be chosen from Table V. 8-hydroxyquinoline-β-D-glucuronide produces a dark color in the presence of Bgluc and would be the preferred choice of substrate. A metallic salt such as ferric ammonium citrate is also added to form a black water insoluble complex consisting of ferric ions and the aglycone released when the substrate is hydrolized by glucuronidase from *E. coli*.

With further reference to Table IV, Bgal, Bfuc and Bglu are common to Aeromonas and general coliforms. However, as indicated in Table IV, Bgal, Bfuc and Bglu are not generally produced by Salmonella or Shigella. Therefore, a substrate can be selected from Table V which reacts with one of Bgal, Bfuc and Bglu to produce a second distinct color. 6-chloro-3-indolyl-β-D-galactopyranoside produces a pink color in the presence of Bgal and is selected as the second substrate.

Optionally, the 6-chloro-3-indolyl-β-D-galactopyranoside can be replaced with 5-bromo-6-chloro-3-indolyl-β-D-galactopyranoside so that Aeromonas and general coliform colonies show as teal instead of pink.

As noted, the second substrate selected will result in colonies of Aeromonas also showing as a generally red-pink color. To avoid growth of Aeromonas colonies, an inhibitor, preferably nalidixic acid, is added. Thus, colonies of *E. coli* will show as substantially black, whereas colonies of general coliforms will show as a red-pink color.

Example XII

The selected microorganisms to be detected, quantified and differentiated in this example are *E. coli,* general coliforms and Aeromonas spp. as a substantially black color and Salmonella or Shigella spp. as a second distinct color. The first substrate selected is 8-hydroxyquinoline-β-D-galactoside, which results in colonies of *E. coli,* general coliforms and Aeromonas showing as substantially black. The second substrate chosen can be either 5-Bromo-4-chloro-3-indolyl-α-D-galactopyranoside or 6-chloro-3-indolyl-α-D-galactopyranoside. If the former of these two substrates is chosen, colonies of Salmonella or Shigella will show as a teal color, whereas if the latter of the two aforementioned substrates is chosen, colonies of Salmonella or Shigella will show as a red-pink color.

Optionally, in this example, Aeromonas may be eliminated by adding an inhibitor, preferably nalidixic acid, as discussed in detail above.

Example XIII

The selected microorganisms to be detected, quantified and differentiated in this example are the same as in Example 1, except that this example illustrates a correction for false positives. That is, it is possible that certain unusual Enterobacter and Klebsiella spp. will show as black colonies along with *E. coli* in the test medium disclosed in Example 1. Thus, the count of *E. coli* could be inaccurately high.

In this example, 4-methyl-umbrelliferyl-β-D-xylopyranoside is added to the test medium described in Example 1. In so doing, Enterobacter and Klebsiella spp. showing as black colonies will also fluoresce, thereby allowing reduction in the false positive count of *E. coli*. This example illustrates the flexibility of embodiments incorporating the present invention. The fluoroescent component does not interfere with the substantially black color so that the black colonies are easily distinguished with the naked eye. Yet, under ultraviolet light, false positives can be detected and substantially reduced by examining the black colonies for fluorescence.

Example XV

The selected microorganisms to be detected, quantified, differentiated and identified are *E. coli* as a substantially black color and Salmonella spp. as pink-red. General coliforms are colorless in this example.

With reference to Example I, *E.Coli* is responsive to 8-hydroxy-quinoline-β-D-glucuronide. General coliforms, Salmonella, Shigella and Aeromonas are not responsive to 8-hydroxy-quinoline-β-D-glucuronide. Thus, the first substrate chosen is 8-hydroxy-quinoline-β-D-glucuronide.

With reference to table IV, esterase enzyme is positive for Salmonella spp., but not any of the other preferred microorganisms to be detected. With reference to table V, the substrate 6-chloro-3-indolyl-caprylate can be identified, and will produce a pink-red color upon cleavage, and is therefore chosen as the second substrate.

In this test medium, colonies of *E. coli* will show as substantially black and colonies of Salmonella or Shigella will show as pink-red.

Example XV

The selected microorganisms to be detected, quantified, differentiated and identified are *E. coli* as a substantially black color, Salmonella spp. as dark blue-purple, and general coliforms as red-pink.

With reference to Example I, *E. coli* is responsive to 8-hydroxy-quinoline-β-D-glucuronide. General coliforms, Salmonella, Shigella and Aeromonas are not responsive to 8-hydroxy-quinoline-β-D-glucuronide. Thus, the first substrate chosen is 8-hydroxy-quinoline-β-D-glucuronide.

With reference to tables IV and V, 5-bromo-4-chloro-3-indolyl-caprylate can be identified as the second substrate to which Salmonella or Shigella will be responsive. With further reference to Table V, 5-bromo-4-chloro-3-indolyl-caprylate forms a teal color upon cleavage.

6-chloro-3-indolyl-α-D-galactopyranoside, which produces a pink-red color upon cleavage, is chosen as the third substrate to which *E.coli* general coliforms and Salmonella or Shigella are responsive.

In this example, *E. coli* colonies show as substantially black, general coliform colonies show as red-pink, and Salmonella/Shigella show as blue-violet (=red-pink+teal).

Example XVI

The selected microorganisms to be detected, quantified and differentiated in this example are *E. coli* as a substantially black color and general coliforms as a second distinct color.

With reference to Table IV, *E. coli* produces the enzyme Bgluc, and Bgluc is not produced by any of the other microorganisms desired to be detected. Therefore, a substrate which produces a distinct color upon cleavage of Bgluc should be chosen from Table V. 8-hydroxyquinoline-β-D-glucuronide produces a dark color in the presence of Bgluc and would be the preferred choice of substrate. A metallic salt such as ferric ammonium citrate is also added to form a black water insoluble complex consisting of ferric ions and the aglycone released when the substrate is hydrolized by glucuronidase from *E. coli*.

With further reference to Table IV, Bgal, Bfuc and Bglu are common to Aeromonas and general coliforms. However, as indicated in Table IV, Bgal, Bfuc and Bglu are not generally produced by Salmonella/Shigella. Therefore, a substrate can be selected from Table V which reacts with one of Bgal, Bfuc and Bglu to produce a second distinct color. 5-bromo-4-chloro-3-indolyl-β-D-galactopyranoside can be chosen as the second substrate, in which event colonies of *E. coli* will appear as substantially black and general colifom colonies will appear as teal. Optionally, 5-bromo-6-chloro-3-indolyl-galactopyranoside can be chosen as the second substrate, in which event colonies of *E. coli* will appear as substantially black and general colifom colonies will appear magenta. To avoid growth of Aeromonas colonies, an inhibitor, preferably nalidixic acid, is added. Thus, colonies of *E. coli* will show as substantially black, whereas colonies of general coliforms will show as a magenta color.

Although several broad examples which incorporate the present invention have been described above, it is to be understood that the present invention is not to be limited by the examples disclosed herein. Indeed, the disclosure and examples above teach one of ordinary skill a virtually limitless number of test media which would be within the scope of the claims appended hereto.

Further, while this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for detecting, quantifying, and differentiating colonies of Aeromonas from selected other biological entities in a test sample, said method comprising the following steps: providing a base medium including ions of a salt, a β-D-galactoside substrate that forms a first component of a first color in the presence of a first enzyme, and an α-D-galactoside substrate that forms a second component of a second color distinguishable from said first color in the presence of a second enzyme; inoculating the test medium with a test sample; incubating the test medium; and examining the test medium whereby aggregations of colonies of Aeromonas are indicated by said first color, and aggregations of colonies of Salmonella are indicated by said second color, and whereby colonies of general coliforms are indicated by a third color, said third color being a combination of said first and second colors.

2. The method as set forth in claim 1, whereby colonies of *E. coli* are also indicated by said third color.

3. The method as set forth in claim 2, wherein said β-D-galactoside substrate d said α-D-galactoside substrates are chromogenic substrates.

\* \* \* \* \*